(12) United States Patent
Brooks et al.

(10) Patent No.: US 6,238,595 B1
(45) Date of Patent: May 29, 2001

(54) TARGET FOR TESTING PERFORATING SYSTEMS

(75) Inventors: James E. Brooks, Manvel; Wenbo Yang, Sugar Land, both of TX (US)

(73) Assignee: Schlumberger Technology Corp., Sugar Land, TX (US)

( * ) Notice: Subject to any disclaimer, the term of this patent is extended or adjusted under 35 U.S.C. 154(b) by 0 days.

(21) Appl. No.: 09/024,540

(22) Filed: Feb. 17, 1998

(51) Int. Cl.[7] .............................. G01N 3/30; C04B 38/04
(52) U.S. Cl. ................................ 252/408.1; 73/152.01; 73/865.6; 501/133; 106/737; 106/738
(58) Field of Search ..................... 252/408.1; 166/250.1, 166/250.09; 73/152.01, 865.6; 106/737, 738; 501/133

(56) References Cited

U.S. PATENT DOCUMENTS

| | | | |
|---|---|---|---|
| 757,483 | * 4/1904 | McClenahan | 106/97 |
| 4,304,122 | * 12/1981 | Tentor | 73/865.6 |
| 4,353,746 | * 10/1982 | Birchall et al. | 106/89 |
| 4,430,889 | * 2/1984 | Sutton | 73/865.6 |
| 4,518,508 | * 5/1985 | Conner | 210/751 |
| 5,569,320 | * 10/1996 | Sasaki et all | 106/287.26 |

OTHER PUBLICATIONS

American Petroleum Institute, RP 43: Evaluation of Well Perforators, Section 1 Evaluation of Perforating Systems Under Surface Conditions, Concrete Targets, Edition 5, 9–10 (Jan. 1991).*

American Society for Testing and Materials, Standard Specification for Concrete Aggregates, 1–7 (Dec. 1993).*

* cited by examiner

Primary Examiner—Robert J. Warden, Sr.
Assistant Examiner—Kaj K. Olsen
(74) Attorney, Agent, or Firm—Trop, Pruner & Hu P.C.

(57) ABSTRACT

A target for testing perforating systems, including an agglomeration of sand selected and conditioned to simulate a down-hole rock formation. A sand mixture may be selected to simulate the distributions of particle size, density and hardness of the down-hole rock formation. The sand may be agglomerated in the presence of a binding agent. Conditioning of the target may be conducted to simulate the compressive strength and porosity of the down-hole rock formation.

33 Claims, 4 Drawing Sheets

TARGET FOR TESTING PERFORATING SYSTEMS

BACKGROUND

The invention relates to a target for testing perforating systems.

After a well has been drilled and casing has been cemented in the well, one or more portions of the casing adjacent pay zones are perforated to allow fluid from the surrounding formation to flow into the well for production to the surface. Perforating guns may be lowered into the well and the guns fired to create openings in the casing and to extend perforations into the surrounding formation. The firing of a perforating gun generally refers to exploding a shaped charge within a well. Several systems and techniques are available for firing perforating guns, including percussion-, pressure-, and electrically-actuated systems.

The characteristics (e.g., shape, diameter, depth, etc.) of the perforations created in the surrounding rock formation is a key determinant of well-flow performance. These characteristics may be referred to as the perforation characteristic of the rock formation, or of a simulated rock formation, whichever the case may be. To obtain data relating to such perforation characteristics, surface tests may be performed in which a perforating gun is fired into a test target representing the rock formation in the well where the gun will be fired. The most common type of perforating gun target is manufactured from concrete, such as the target defined by API RP 43, Edition 5, Section 1 ("API specification").

The concrete-type target is typically made from about 50% by volume sand. The API specification calls for sands to be used that qualify under ASTM Designation C33–67, which relates to the distribution of particle size in the sand, as shown below in Table 1.

TABLE 1

| U.S. Mesh | (mm) | Percent Passing | Percent Retained |
|---|---|---|---|
| ⅜ in. | 9.5 | 100 | 0 |
| No. 4 | 4.8 | 95–100 | 0–5 |
| No. 8 | 2.4 | 80–100 | 0–20 |
| No. 16 | 1.2 | 50–85 | 15–50 |
| No. 30 | 0.59 | 25–60 | 40–75 |
| No. 50 | 0.30 | 10–30 | 70–90 |
| No. 100 | 0.15 | 2–10 | 90–98 |
| Pan | <0.15 | 0 | 100 |

In addition to use of a concrete-type target, another method of preparing a target for testing perforating guns is to obtain an actual sample of rock to represent the rock formation in the well ("down-hole rock formation"). To obtain this type of target, a near-surface or otherwise accessible rock formation must be located to represent the down-hole rock formation, and then a target sample must be quarried. This method of testing a perforating gun is substantially more expensive than constructing a concrete-type target. Also, depending on the availability and homogeneity of a given rock formation for constructing targets, it may be difficult under this method to reproduce testing results due to variation in the characteristics of the quarried rock formation.

SUMMARY

In general, in one aspect, the invention features a target for testing perforating systems, including an agglomeration of rock particles and a removable binding agent.

In general, in another aspect, the invention features a mixture for manufacturing perforating system targets, including a mixture of two sizes of sand particles having a 1:10 ratio in size, where the smaller particles are about 10% of the sand, and the mixture has a bulk density of about 80%.

In general, in another aspect, the invention features a method for manufacturing a target for testing perforating systems, where a mixture of sand particles is selected to simulate a down-hole rock formation; the sand mixture is agglomerated; and the agglomeration is conditioned to simulate the down-hole rock formation.

In general, in another aspect, the invention features a method for manufacturing a target for testing perforating systems, where a slurry is formed of sand particles with a melted binding agent, the slurry is injected into a target mold and then cooled to solidify the binding agent, and the binding agent is then removed from the target.

Other features will become apparent from the following description and from the claims.

DETAILED DESCRIPTION

When a perforating system is used in a well, generally shaped charges are lowered into the well and fired into the surrounding rock formation. Typically, the well will be lined with casing, and will be full of fluid, so that the shaped charge is fired in the fluid.

Figure 1:
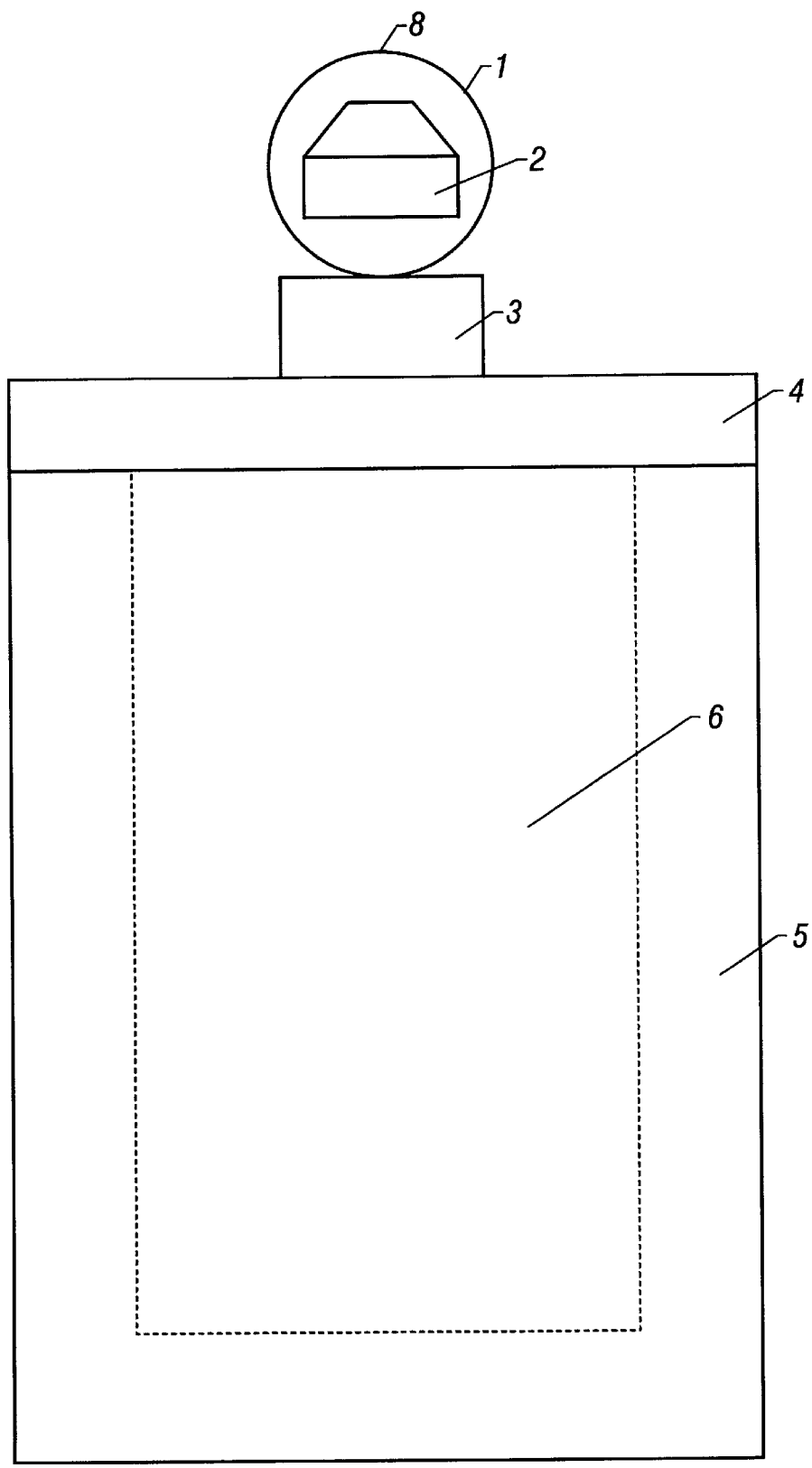
FIG. 1 is a diagram of a target for testing perforating systems, according to an embodiment of the present invention.

Referring to FIG. 1, an exemplary test system is shown where a target may be used to test a perforating system. The perforating system 1 can include a container housing 8 in which one or more shaped charges 2 are loaded. This type of perforating gun is a through-tubing gun. Alternatively, other types of perforating guns can also be used. A water clearance vessel 3 is positioned to simulate water within a well through which the perforating jet of the shaped charge 2 must pass. Beneath the water clearance vessel 3, a casing plate 4 typically formed of steel or a steel alloy is positioned to simulate the casing through which the shaped charge 2 would pass when fired in the well. Beneath the casing plate 4, a target 6 is positioned within a metal sleeve 7. When the perforating system 1 is fired, the perforating jet of the shaped charge 2 passes through the water clearance vessel 3 and the casing plate 4 into the target 6. The sleeve 5 prevents the target 6 from splitting as the shaped charge 2 passes into it.

Although the perforating gun 1, water vessel 3, casing plate 4, and target 6 are shown in FIG. 1 as being arranged vertically, other arrangements are also possible, including a horizontal or slanted arrangement.

In one embodiment of the present invention, a mixture is compressed to form an artificial rock target. In the context of the present invention, the target may be referred to as an agglomeration, that is, a cohesive mass of particles. Thus, in the context of the present invention, agglomerating refers to any process through which a mixture of particles may be formed into a cohesive mass. The mixture used to form the target is selected to simulate the rock formation that the target will represent. The mixture may include any size rock particles, including sand particles, according to the rock formation being simulated. A binding agent such as cement may be included in the mixture to promote adhesion of the mixture. The target may then be conditioned through a sintering process, where the target is heated to further promote adhesion of particles within the target.

Figure 2:
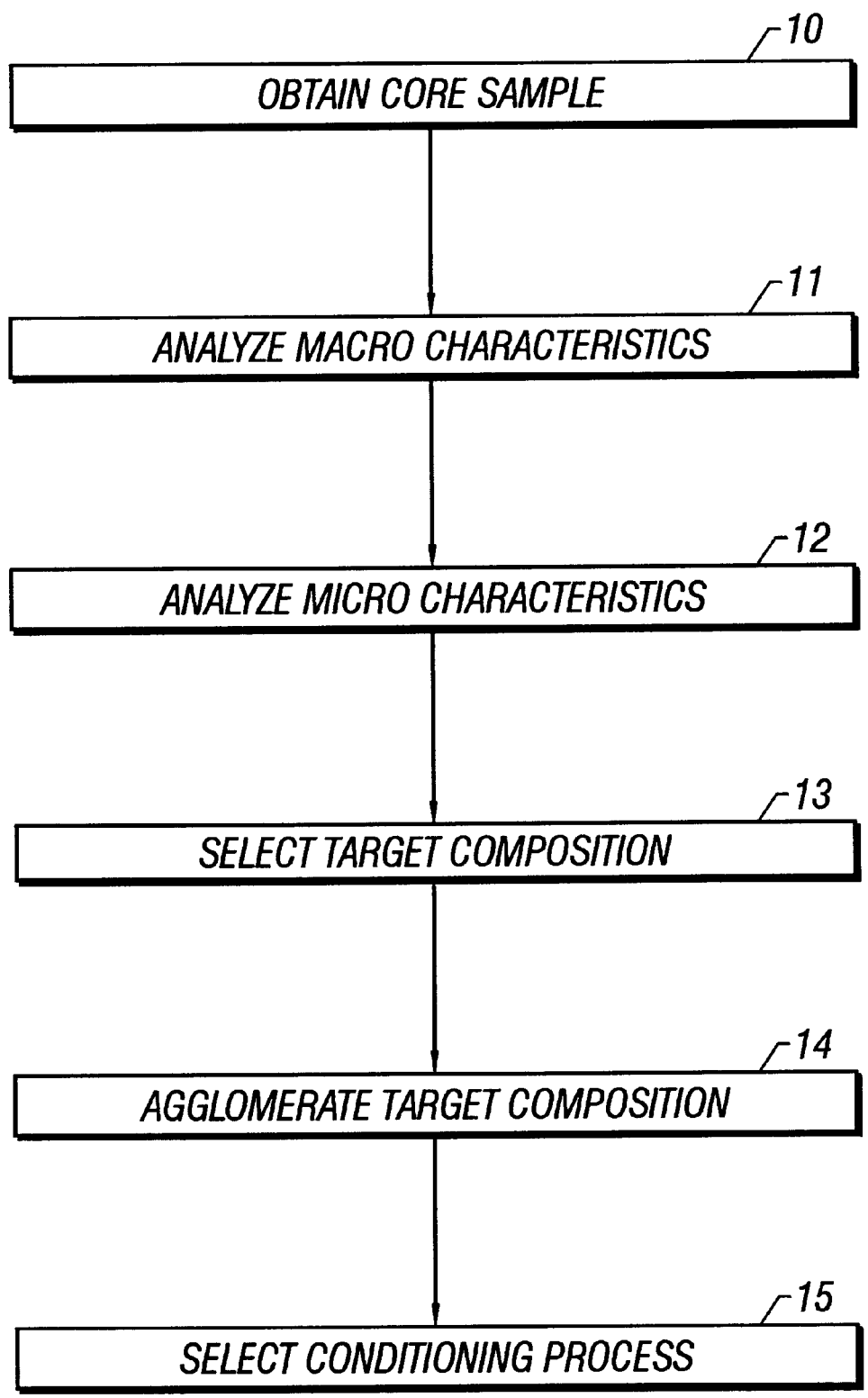
FIG. 2 is a flow diagram showing construction of a target for testing perforating systems, according to an embodiment of the present invention.

Referring to FIG. 2, a flow diagram illustrates a method of manufacturing targets according to an embodiment of the present invention. In the first step 10, a core sample is obtained from a well that represents the rock formation that a perforating system will be fired into. Next, at step 11, the core sample is analyzed to determine its compressive strength and porosity. These properties may be referred to as macro characteristics of the core sample, because they pertain to the sample as a whole and not to the individual particles the core sample may contain. In the next step 12, the core sample is analyzed to determine its mineralogy, that is, what it is made of and what are the distributions of size, density, and hardness among the individual particles that form the core sample. In the context of the present invention, hardness refers to measurements taken according to the Mohs' scale of hardness. The mineralogy properties may be referred to as the micro characteristics of the core sample, because they pertain to the individual particles that make up the core sample.

Based on the data obtained from analysis of the core sample, a mixture is then selected at step 13 for use in manufacturing the target. In one embodiment, the mixture can be selected to provide a target that will have the same or similar mineralogy characteristics as the core sample. In another embodiment, the mixture may be selected to provide a target that will have different mineralogy characteristics from the core sample, but that will nevertheless allow penetration comparable to the rock formation represented by the core sample.

At step 14, the mixture is agglomerated to form a target. It is preferred that agglomeration be conducted in a target molding cavity to form cylindrical targets having a predetermined diameter (e.g., 4 inches), and a predetermined length (e.g., 36 inches). Targets having other shapes can also be formed. According to one embodiment, a compression technique is used in which the mixture is placed in a cavity and the mixture is compressed using a hydraulic mechanism. In another embodiment, agglomeration is achieved through injection molding.

At step 15, the agglomerated mixture is conditioned to achieve a desired combination of compressive strength and porosity. If the compression technique is used, steps 14 and 15 may actually be combined. The amount of compression depends on the desired characteristics of the target. A high-temperature sintering process may also be used to condition the target. Operating parameters of the sintering process will depend on the desired characteristics of the target.

Figure 3:
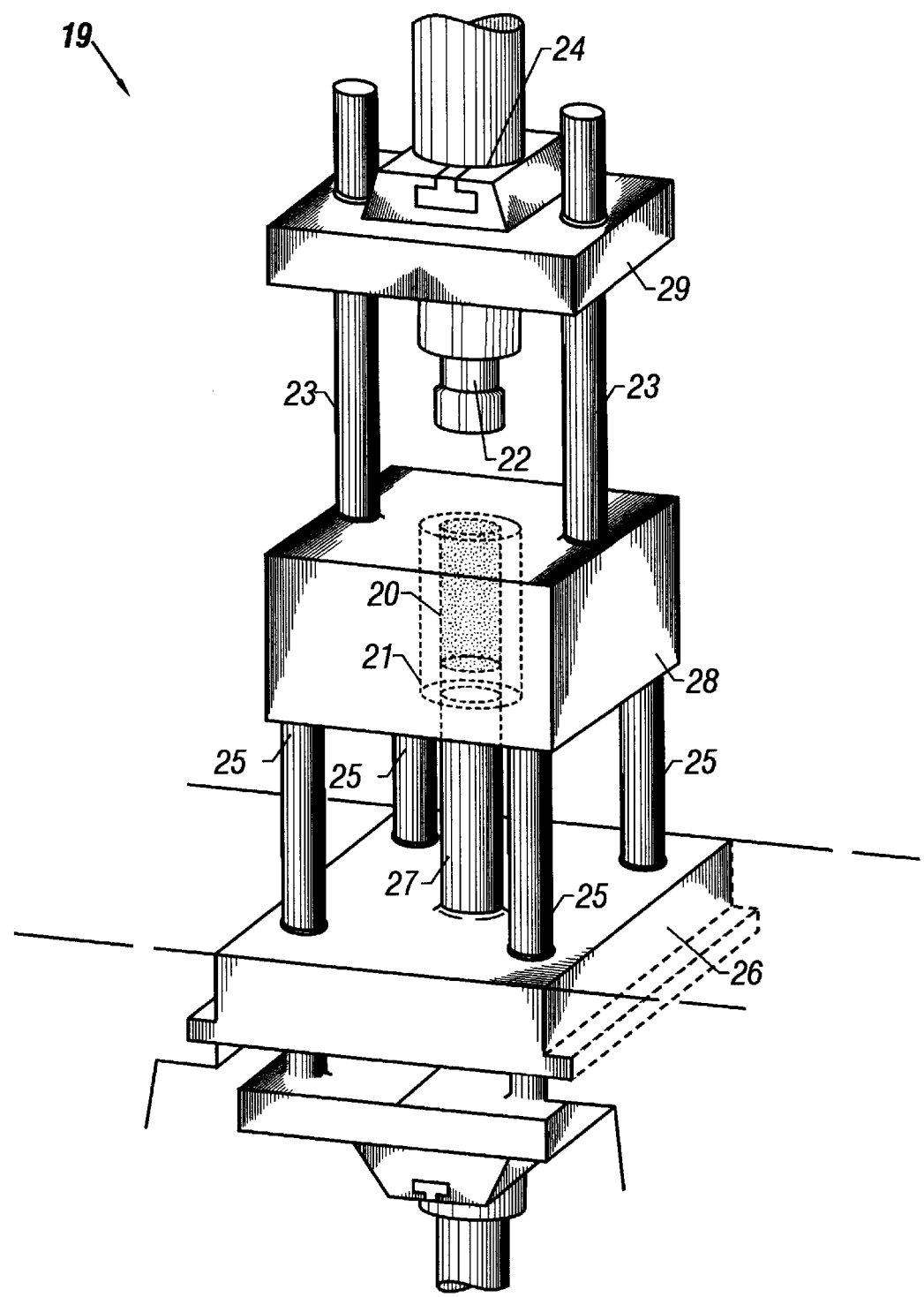
FIG. 3 is a diagram of a process for making a target by compression, according to an embodiment of the present invention.

Referring to FIG. 3, an apparatus 19 is shown for making a target by compressing a mixture 20 in a hydraulic die 28, according to an embodiment of the present invention. The mixture 20 can include particles of sand and a binding agent, which is placed into the cavity 21 of a die 28. The cavity 21 is generally cylindrical in shape. The die 28 is supported by support members 25 that are attached to and seated in a support plate 26. The mixture 20 sits on a rod 27 that forms the bottom face of the cavity 21. Above the cavity 21 is arranged a punch 22 that is moveable up and down vertically by a hydraulic mechanism (not shown). The punch 22 slides through the bore 24 of a top plate 29 that is supported by members 23 mounted on the die 28. During operation, after the mixture 20 is placed into the cavity 21, the punch 22 is forced into the die 21 to compress the mixture 20.

Figure 4:
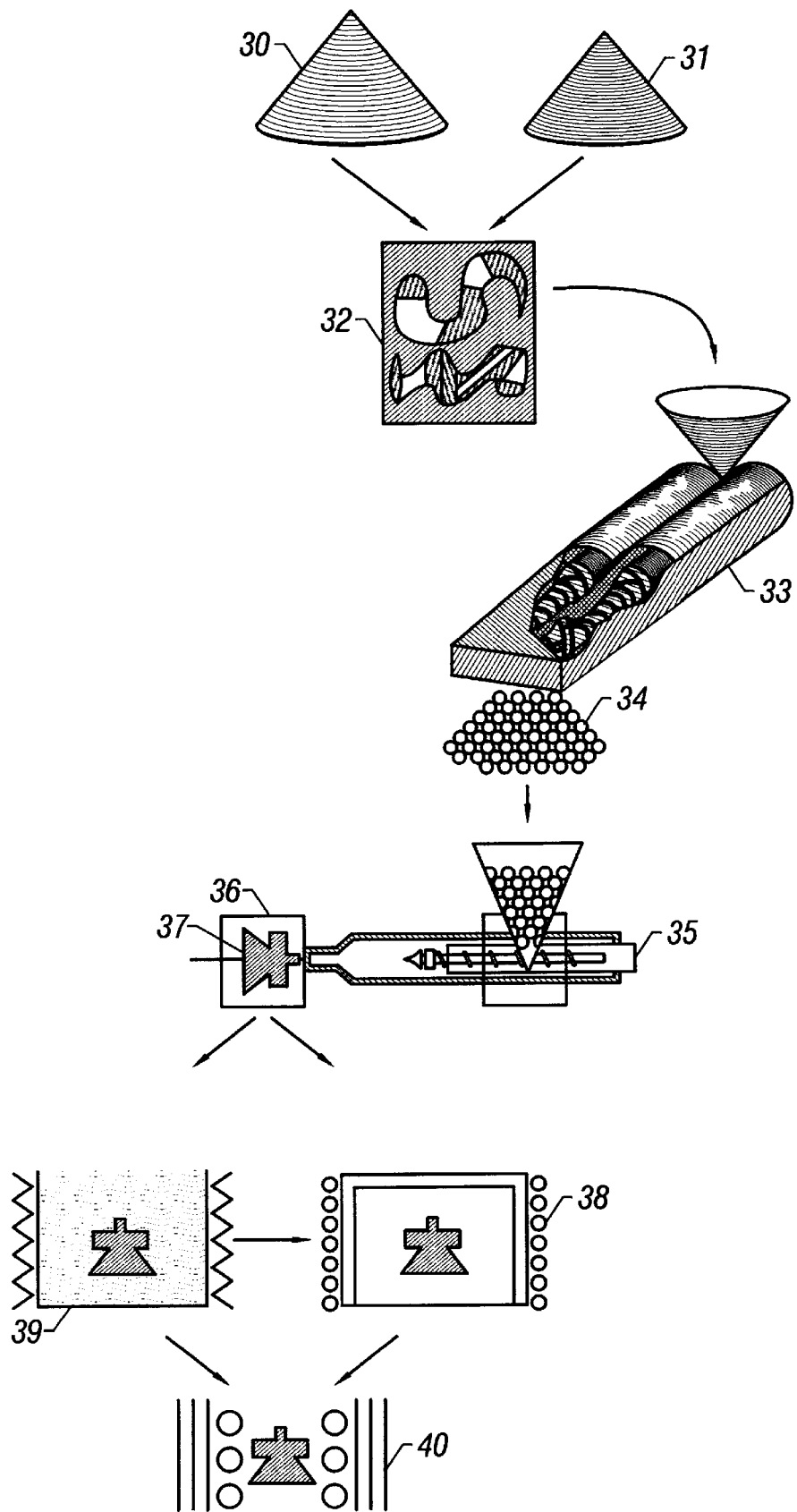
FIG. 4 is a diagram of an injection molding process for making a target for testing perforating systems, according to an embodiment of the present invention.

Referring to FIG. 4, a process is presented for making a target through injection molding, according to an embodiment of the present invention. A collection of sand particles 30 and a binding agent material 31 are premixed 32. In one embodiment, the premixing 32 may be conducted at an elevated temperature sufficient to melt the binding agent 31 form a slurry of sand and melted binding agent. In the next step of the process, the combined sand particles 30 and binding agent 31 are placed in pelletizer 33 to form generally homogenous pellets 34. The pellets 34 are then placed in an injection molding device 35 that forces the pellets 34 into a target mold 36. After the target 37 is allowed to cool, it is removed from the target mold 36, and subjected to a process where the binding agent 31 is removed from the target 37. This process can be a heating process 38, or a chemical process 39. In one embodiment, the target may then be subjected to a sintering process 40 to increase the compressive strength of the target.

Binding agents used to practice the present invention may include any material that promotes the agglomeration of the mixture used to form the target. Suitable binding agents include, for example, waxes, polymers, clays, and cements. The binding agent makes up some percentage of the mixture used to form the target, such as under about 10% (e.g., about 2–8%).

Where it is desired to form a target from a sand having a bulk density of approximately 80%, a mixture of sand having two grain sizes can be selected, where the grain sizes have a predetermined ratio in average size, and the mixture contains about 10% by weight of the smaller size grains.

Other embodiments are also within the scope of the following claims. Although the present invention has been described with reference to specific exemplary embodiments, various modifications and variations may be made to these embodiments without departing from the spirit and scope of the invention as set forth in the claims.

What is claimed is:

1. A target used for testing a perforating system, comprising:

a mixture of rock particles that are bound together with a preselected amount of binding material, the rock particles distributed between at least two distinct groups of two general sizes having a preselected ratio to provide a predetermined perforation characteristic that is similar to the perforation cbaracteristic of a down-hole rock formation.

2. The target of claim 1, wherein the binding material is selected from the group consisting of wax, polymer, clay, and cement.

3. The target of claim 1, wherein the rock particles includes 90% by weight of quartz.

4. A target for testing perforating systems, comprising:

an agglomeration of sand particles and a removable binding agent, the sand particles distributed between at least two distinct groups of two general sizes having a preselected ratio to provide a penetration characteristic of a down-hole rock formation, the penetration characteristic relating to firing a perforating system into the rock formation.

5. The target of claim 4, wherein the binding agent comprises wax, polymer, clay, or cement.

6. The target of claim 4, wherein the sand is composed of at least 90% by weight of quartz.

7. The target of claim 4, wherein the agglomeration comprises a sintered adhesion of sand particles.

8. A mixture for manufacturing perforating system targets, comprising smaller size rock particles and larger size rock particles, the sizes having about a 1:10 ratio in average size, the mixture comprising smaller size rock particles that are about 10% by weight of the mixture, and the mixture having a bulk density of about 80%, the mixture selected to have at least one of a perforation characteristic and a penetration characteristic similar to that of a down-hole formation.

9. A method for manufacturing a target for testing perforating systems, comprising:

selecting a mixture of sand particles distributed between at least two distinct groups of two general sizes to simulate at least one of a perforation characteristic and a penetration characteristic of a down-hole rock formation;

agglomerating the mixture of sand particles; and conditioning the agglomeration to simulate the down-hole rock formation.

10. The method of claim 9, wherein the sand particles are agglomerated through compression.

11. The method of claim 9, wherein the sand particles are agglomerated in the presence of a binding agent.

12. The method of claim 11, wherein the binding agent comprises a material selected from the group consisting of wax, polymer, clay and cement.

13. The method of claim 11, wherein the amount of binding agent in the mixture is under 10% by weight.

14. The method of claim 11, further comprising removing the binding agent after agglomeration.

15. The method of claim 14, wherein the binding agent is removed by a heating process.

16. The method of claim 14, wherein the binding agent is removed by a chemical process.

17. The method of claim 9, further comprising selecting the mixture of sand particles to simulate the distribution of particle size, density and hardness of a down-hole rock formation.

18. The method of claim 9 wherein the mixture comprises two groups which have a 1:10 ratio in average size of particles with respect to each group, the group comprising the smaller particles are about 10% by weight of the mixture, and the mixture having a bulk density of about 80%.

19. The method of claim 9, wherein the conditioning is performed to simulate the compressive strength and porosity of the down-hole rock formation.

20. The method of claim 9, wherein the conditioning comprises compressing the agglomeration.

21. The method of claim 9, wherein the conditioning comprises sintering the agglomeration.

22. A product made in accordance with the method of claim 9.

23. A method for manufacturing a target for testing perforating systems, comprising:

selecting a mixture of sand particles from at least two distinct groups of two general sizes having a preselected ratio to simulate at least one of a perforation characteristic and a penetration characteristic of a down-hole rock formation;

forming a slurry of the sand particles with a melted binding agent;

injecting the slurry into a target mold;

cooling the slurry to solidify the melted binding agent; and removing the binding agent.

24. The method of claim 23, wherein the binding agent is selected from the group consisting of waxes and polymers.

25. The method of claim 23, wherein the slurry comprises about 2–8% by weight of binding agent.

26. The method of claim 23, wherein the binding agent is removed by a heating process.

27. The method of claim 23, wherein the binding agent is removed by a chemical process.

28. The method of claim 23, further comprising selecting the mixture of sand particles to simulate the distribution of particle size, density and hardness of a down-hole rock formation.

29. The method of claim 23, further comprising conditioning the target after the binding agent is removed to simulate the down-hole rock formation.

30. the method of claim 29, wherein the conditioning is performed to simulate the compressive strength and porosity of the down-hole rock formation.

31. The method of claim 29, wherein the conditioning comprises compressing the agglomeration.

32. The method of claim 29, wherein the conditioning comprises sintering the agglomeration.

33. A product made in accordance with the method of claim 23.

* * * * *